US009408888B2

(12) United States Patent
Dhar et al.

(10) Patent No.: US 9,408,888 B2
(45) Date of Patent: Aug. 9, 2016

(54) HIGH AFFINITY BIVALENT HELICALLY CONSTRAINED PEPTIDE AGAINST CANCER

(75) Inventors: Amlanjyoti Dhar, Kolkata (IN); Shampa Mallick, Kolkata (IN); Israr Ahmed, Kolkata (IN); Aditya Konar, Kolkata (IN); Santu Bandyopadhyay, Kolkata (IN); Siddhartha Roy, Kolkata (IN)

(73) Assignee: COUNCIL OF SCIENTIFIC AND INDUSTRIAL RESEARCH, New Delhi (IN)

(*) Notice: Subject to any disclaimer, the term of this patent is extended or adjusted under 35 U.S.C. 154(b) by 0 days.

(21) Appl. No.: 13/980,701

(22) PCT Filed: Jan. 30, 2012

(86) PCT No.: PCT/IB2012/050409
§ 371 (c)(1),
(2), (4) Date: Sep. 26, 2013

(87) PCT Pub. No.: WO2012/104766
PCT Pub. Date: Aug. 9, 2012

(65) Prior Publication Data
US 2014/0155331 A1    Jun. 5, 2014

(30) Foreign Application Priority Data
Jan. 31, 2011    (IN) .............................. 207/DEL/2011

(51) Int. Cl.
*A61K 38/16* (2006.01)
*A61K 38/10* (2006.01)
*A61K 9/00* (2006.01)
*C07K 14/47* (2006.01)
*A61K 45/06* (2006.01)
*C07K 14/00* (2006.01)

(52) U.S. Cl.
CPC .............. *A61K 38/16* (2013.01); *A61K 9/0019* (2013.01); *A61K 38/10* (2013.01); *A61K 45/06* (2013.01); *C07K 14/00* (2013.01); *C07K 14/47* (2013.01)

(58) Field of Classification Search
None
See application file for complete search history.

(56) References Cited

FOREIGN PATENT DOCUMENTS

WO          03/084475 A2    10/2003
WO    WO 2012104766    *    8/2012

OTHER PUBLICATIONS

R. Banerjee, et al; "Aib-based peptide backbone as scaffolds for helical peptide mimics", J. Peptide Res., vol. 60, Issue 2, pp. 88-94; Aug. 2002.

Jirina Bartkova, et al; "Oncogene-induced senescence is part of the tumorigenesis barrier imposed by DNA damage checkpoints", Nature Letters, vol. 444, Nov. 30, 2006; pp. 633-637.
Flora Brozzi, et al; "S100B Protein Regulates Astrocyte Shape and Migration via Interaction with Src Kinase", The Journal of Biological Chemistry, vol. 284, No. 13, pp. 8797-8811, Mar. 27, 2009.
Debasis Chattopadhyay, et al; "Inactivation of p21 by E1A Leads to the Induction of Apoptosis in DNA-Damaged Cells", Journal of Virology, Oct. 2001, pp. 9844-9856, vol. 75, No. 20.
Brian J. Druker; "Translation of the Philadelphia chromosome into therapy for CML", Blood, Dec. 15, 2008, vol. 112, No. 13, pp. 4808-4817.
Christopher Greenman, et al; "Patterns of somatic mutation in human cancer genomes", Nature, Mar. 8, 2007, vol. 446, No. 7132, pp. 153-158.
Keith G. Inman, et al; "Solution NMR Structure of S100B Bound to the High-affinity Target Peptide TRTK-12", Journal of Molecular Biology, vol. 324, No. 5, Dec. 13, 2002, pp. 1003-1014.
Vasily V. Ivanenkov, et al; "Characterization of S-100b Binding Epitopes", The Journal of Biological Chemistry, vol. 270, No. 24, Issue of Jun. 16, 1995; pp. 14651-14658.
Jirina Bartkova, et al; "DNA damage response as a candidate anti-cancer barrier in early human tumorigenesis", Nature, vol. 434, Apr. 14, 2005, pp. 864-870.
Hironobu Komori, et al; "Regulation of Intracellular Ceramide Content in B16 Melanoma Cells", The Journal of Biological Chemistry, vol. 274, No. 13, Issue Mar. 26, 1999, pp. 8981-8987.
Jing Lin, et al; "Inhibition of p53 Transcriptional Activity by the S100B Calcium-binding Protein", The Journal of Biological Chemistry, vol. 276, No. 37, Issue of Sep. 14, 2001, pp. 35037-35041; Published, JBC Papers in Press, Jul. 13, 2001.
Jing Lin, et al; "Inhibiting S100B Restores p53 Levels in Primary Malignant Melanoma Cancer Cells", The Journal of Biological Chemistry, vol. 279, No. 32, Issue of Aug. 6, 2004, pp. 34071-34077, Published JBC Papers in Press, Jun. 3, 2004.
Jing Lin, et al; "The Calcium-binding Protein S100B Down-regulates p53 and Apoptosis in Malignant Melanoma", The Journal of Biological Chemistry, vol. 285, No. 35, pp. 27487-27498; Aug. 27, 2010; Published JBC Papers in Press, Jun. 29, 2010.
Pingchiang C. Lyu, et al; "α-Helix stabilization by natural and unnatural amino acids with alkyl side chains", Pro. Natl. Acad. Sci., vol. 88, pp. 5317-5320, Jun. 1991.
Ingo Marenholz, et al; "S100 proteins in mouse and man: from evolution to function and pathology (including an update of the nomenclature)", Biochemical and Biophysical Research Communications, vol. 322, pp. 1111-1122; Available online Aug. 20, 2004.

(Continued)

Primary Examiner — Maury Audet
(74) Attorney, Agent, or Firm — Ladas & Parry LLP

(57) ABSTRACT

The present invention describes a novel bivalent helically constrained peptide targeted against S100B that is an effective anti-cancer drug against cancers that over-express S100B. This helix mimetic targeted against S100B induces rapid apoptosis in cancer cells that over-express a calcium binding protein S100B through simultaneous inhibition of key growth pathways including activation of p53.

11 Claims, 14 Drawing Sheets

(56) References Cited

OTHER PUBLICATIONS

Figure 2B:
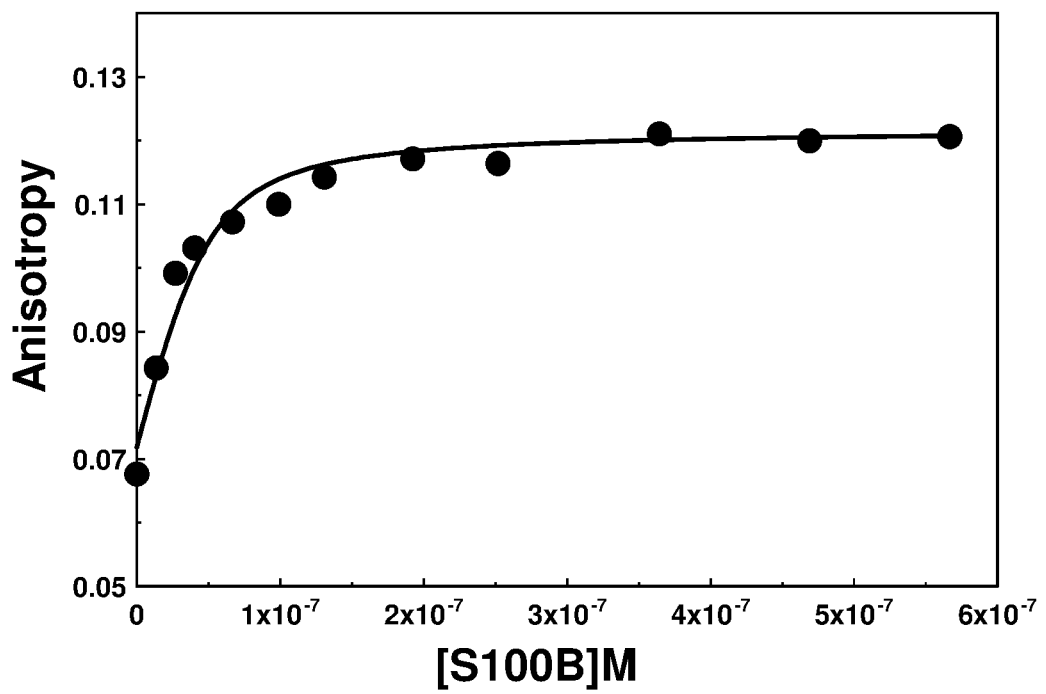

Michael J. Mauro; "Defining and Manging Imatinib Resistance", Hematology American Society of Hematology Education Program, Jan. 1, 2006, vol. 2006, No. 1, pp. 219-225.

Raymond E. Moellering, et al; "Direct inhibition of the NOTCH transcription factor complex", Nature, Nov. 12, 2009; vol. 462(7270); pp. 182-188.

John P. Overington, et al; "How many drug targets are there?", Nature Reviews, vol. 5, Dec. 2006, pp. 993-996.

Richard R. Rustandi, et al; "The $Ca^{2+}$-Dependent Interaction of S100B($\beta\beta$) with a Peptide Derived from p53", Biochemistry, vol. 37, pp. 1951-1960; Published on Web Jan. 30, 1998.

Richard R. Rustandi, et al; "Structural changes in the C-terminus of $Ca^{2+}$-bound rat S100B($\beta\beta$) upon binding to a peptide derived from the C-terminal regulatory domain of p53", Protein Science, vol. 8, pp. 1743-1751; Sep. 1999.

Richard R. Rustandi, et al; "Structure of the negative regulatory domain of p53 bound to S100B($\beta\beta$)", Nature Structural Biology, vol. 7, No. 7, Jul. 2000, pp. 570-574.

Patrick B. Senatus, et al; "Restoration of p53 function for selective Fas-mediated apoptosis in human and rat glioma cells in vitro and in vivo by a p53 COOH-terminal peptide", Molecular Cancer Therapeutics, vol. 5, Issue 1, Jan. 2006, pp. 20-28.

Sanjeev Shangary, et al: "Small-Molecule Inhibitors of the MDM2-p53 Protein-Protein Interaction to Reactive p53 Function: A Novel Approach for Cancer Therapy", The Annual Review of Pharmacology and Toxicology, vol. 49, pp. 223-241; First Published online as a Review in Advanced Oct. 3, 2008.

Evguenia Strom, et al; "Small-molecule inhibitor of p53 binding to mitochondria protects mice from gamma radiation", Nature Chemical Biology, vol. 2, No. 9, pp. 474-479; published online Jul. 23, 2006.

Tom Van Maerken, et al; "Antitumor Activity of the Selective MDM2 Antagonist Nutlin-3 Against Chemoresistant Neuroblastoma With Wild-Type p53", J. Natl. Cancer Inst., vol. 101, Issue 22, Nov. 18, 2009, pp. 1562-1574.

Angelina V. Vaseva, et al; "The mitochondrial p53 pahtway", Biochimica et Biophysics Acta; vol. 1787, pp. 414-420; Available online Oct. 25, 2008.

Lyubomir T. Vassilev, et al; "In Vivo Activation of the p53 Pathway by Small-Molecule Antagonists of MDM2", Science, Feb. 6, 2004, vol. 303; pp. 844-848.

S. Vijayalakshmi, et al; "Comparison of Helix-Stabilizing Effects of $\alpha$, $\alpha$-Dialkyl Glycines with Linear and Cycloalkyl Side Chains", Biopolymers, vol. 53, pp. 84-98; Jan. 2000.

Kurt Wüthrich, et al; "Polypeptide Secondary Structure Determination by Nuclear Magnetic Resonance Observation of Short Proton-Proton Distances", J. Mol. Biol. vol. 180, pp. 715-740, Dec. 15, 1984.

International Search Report mailed May 7, 2012; PCT/IB2012/050409.

\* cited by examiner

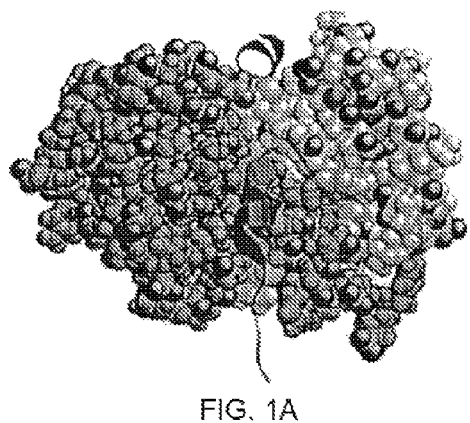
FIG. 1A
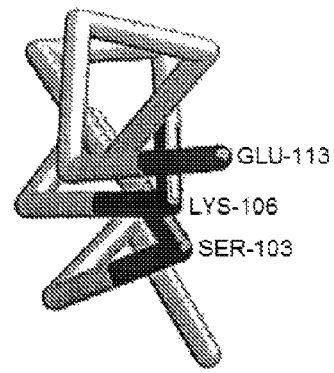
FIG. 1B
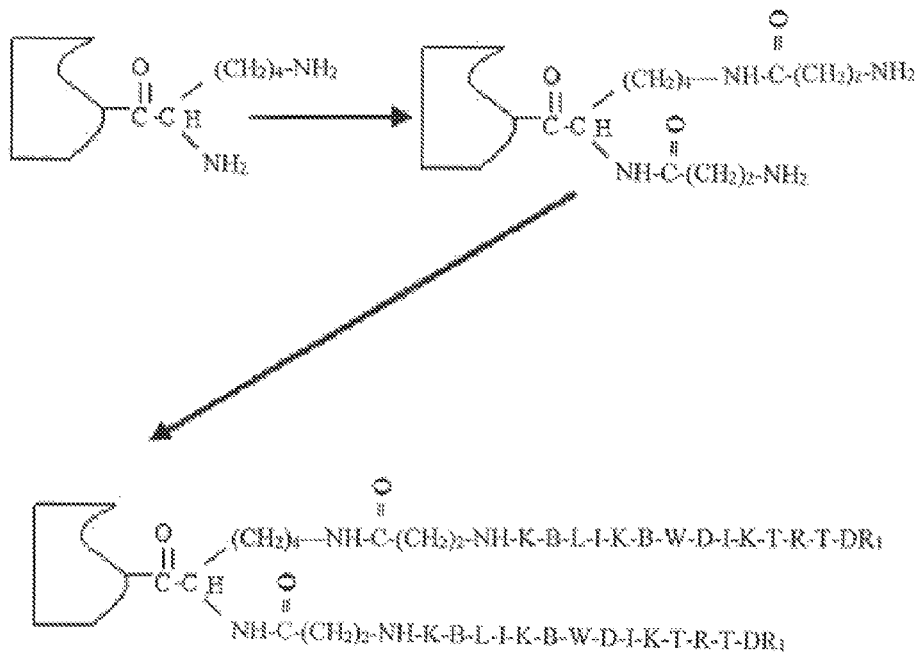
FIG. 1C : Synthesis strategy for SEQ ID No. 3

| Peptidomimetic | Description | Sequence | $K_d$ (nM) |
|---|---|---|---|
| pM-53 | Unsubstituted p53 (375-389) | QSTSRHKKLMFKTEG | ~20000 |
| pBM-53 | Aib substituted p53 | QSTBRHBKLMFKTBG | 4600 ± 1100 |
| pBDC-53 | Cross-linked dimeric Aib substituted p53 | QSTBRHBKLMFKTBGGGCG<br>                                                      \|<br>QSTBRHBKLMFKTBGGGCG | 267 ± 52 |
| pBM-TRTK | Aib substituted TRTK monomeric | TRTKIDWBKILBGGGCG | 300 ± 57 |
| pBDC-TRTK | Cross-linked Dimeric Aib substituted TRTK | TRTKIDWBKILBGGGCG<br>                                       \|<br>TRTKIDWBKILBGGGCG | 32 ± 8.7 |
| pBBD-TRTK | Branched Dimeric Aib substituted TRTK | TRTKIDWBKILBKAbz<br>                             \|<br>                            K<br>                            \|<br>TRTKIDWBKILBKAbz | 7.7±3.5 |

FIG. 2A

Figure 4A:
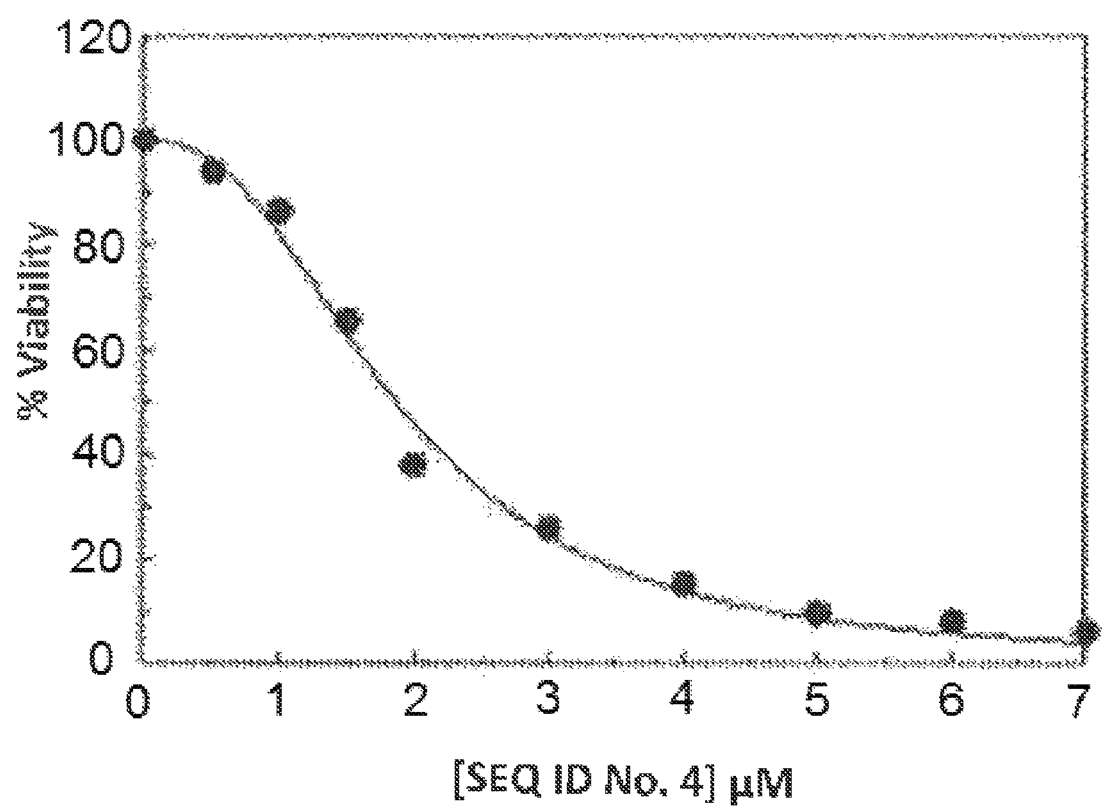

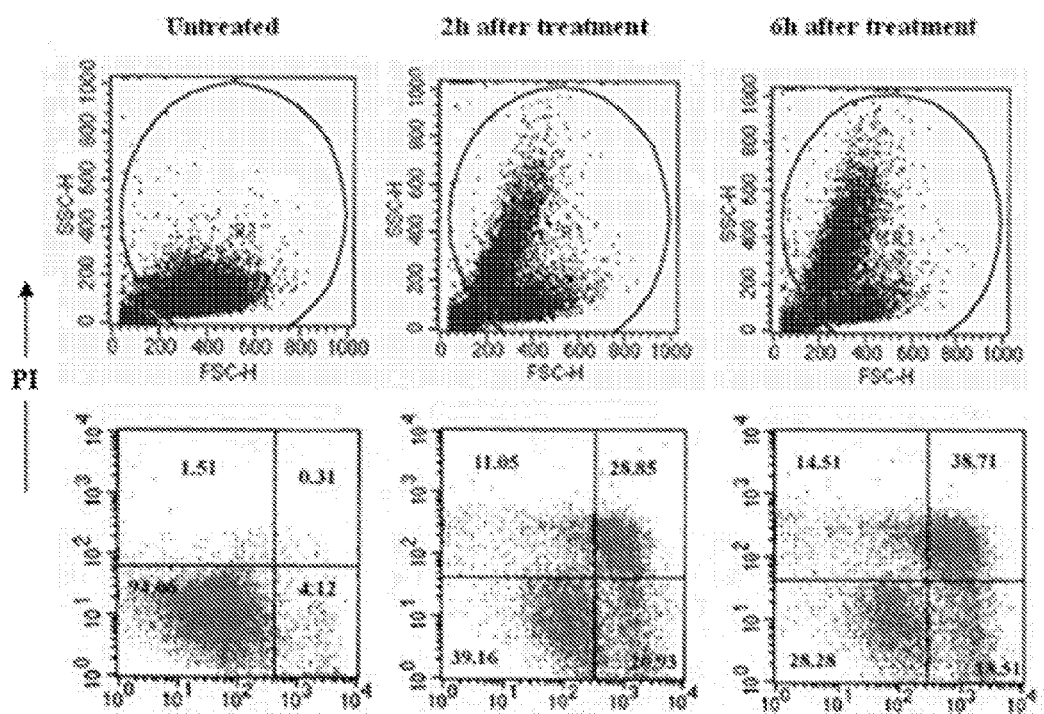
FIG. 4. (B) Flow cytometry of SK-MEL5 cells before and after treatment with 10 microM SEQ ID No 4, using Annexin V and Propidium Iodide (lower panel) and forward/side scatter (upper panel).

A

B

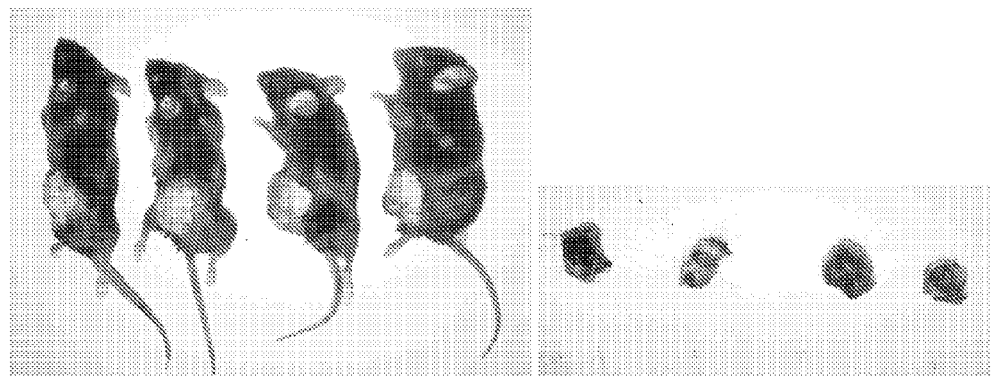
Vehicle treated
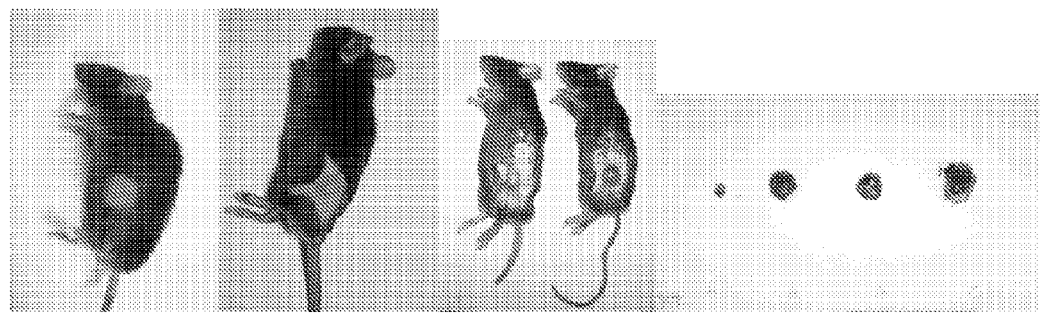
Peptide pBBDR-TRTK treatments (50mg/kg body weight)
Figure 8 Efficacy of the peptidomimatic ( SEQ ID No. 4) in a C57BL/6J melanoma xenograft model as measured by reduced tumor burden in treated animals.

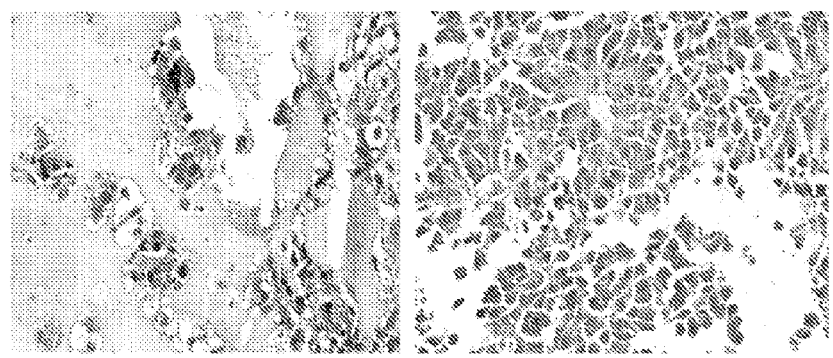
Figure 9: p53 staining of the tumor sections after treatment with 1 dose of 50 mg/Kg of SEQ ID No. 4 (left panel) and vehicle control (right panel).

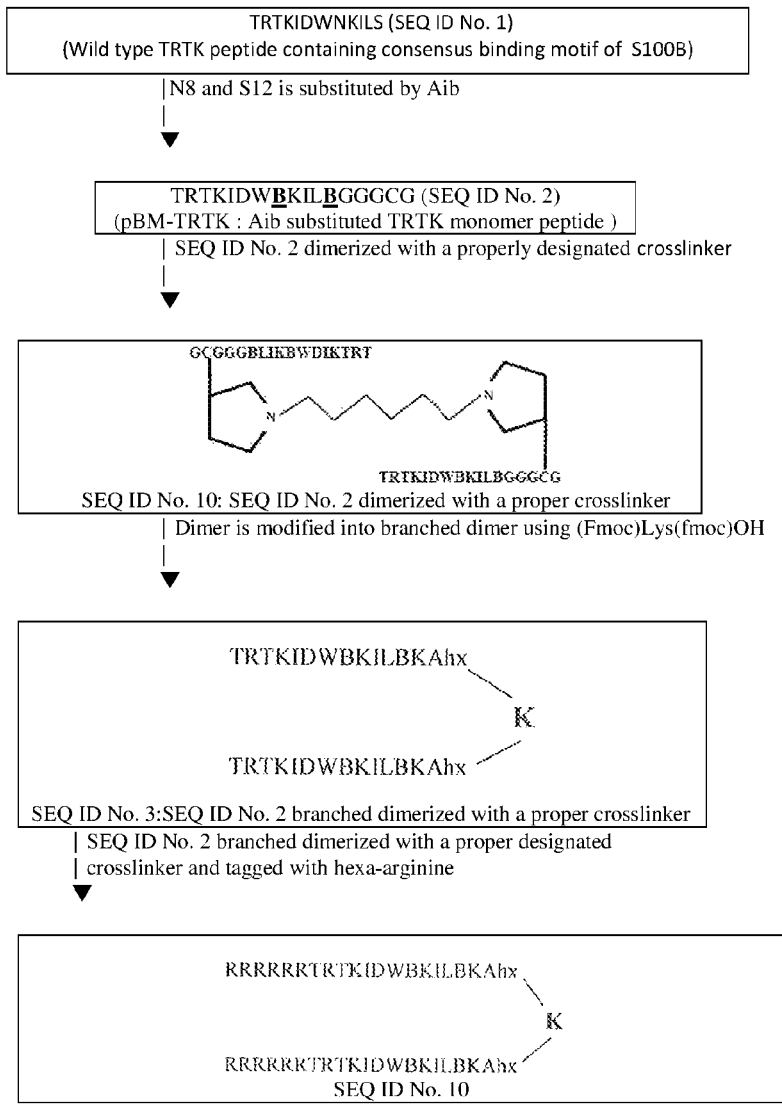
FIG. 10: Flow chart illustrating the process/steps of development of high affinity bivalent peptidomimetics

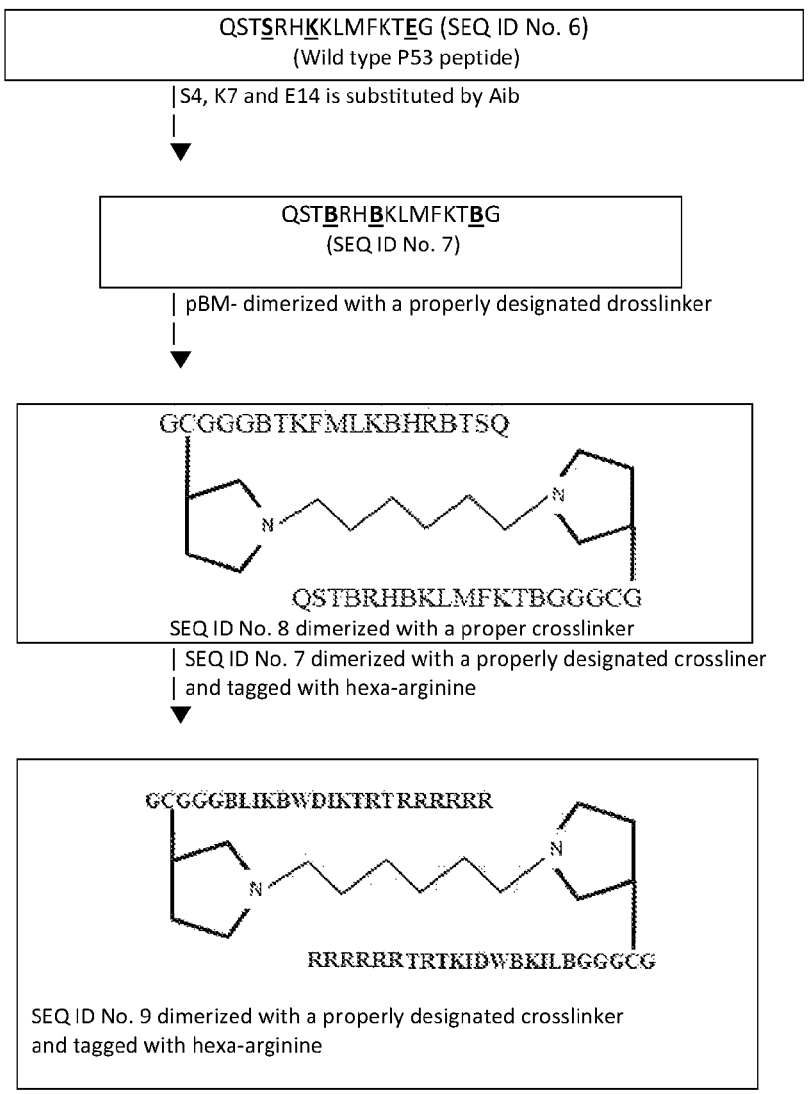
FIG. 11: Flow chart illustrating the process/steps of development of high affinity bivalent peptidomimetics

HIGH AFFINITY BIVALENT HELICALLY CONSTRAINED PEPTIDE AGAINST CANCER

FIELD OF INVENTION

The present invention relates to a novel high affinity bivalent helically constrained peptide against cancer and a process for the preparation thereof. In particular, the present invention relates to the treatment of human cancers having over-expression of S100B and or down-regulation of p53. More specifically, it relates to the treatment of several types of tumors including melanoma and glioma with a new high affinity bivalent helically constrained peptide. This helix mimetic targeted against S100B induces rapid apoptosis in cancer cells that over-express a calcium binding protein S100B through simultaneous inhibition of key growth pathways including activation of p53.

BACKGROUND OF THE INVENTION

Design of specific inhibitors of protein-protein interactions that are capable of turning off specific signaling pathways have an important bearing on the future of therapeutics. Cancer genome project has demonstrated that in many, if not all, tumors accumulate multiple mutations resulting in several dysregulated pathways favoring uncontrolled proliferation (Greenman et al., 2007; Weir et al., 2007). These combinations of dysregulated pathways may be necessary to overcome the multiple tumor suppressor functions present in differentiated cells (Bartkova et al., 2006; Jirina Bartkova, 2005; Weir et al., 2007). Specific targeting of multiple dysregulated pathways, either through a single agent or through multiple agents may provide useful advantage. Thus, drug targets that regulate multiple pathways are important. However, selectivity of inhibited pathways may be crucial to avoid off-target toxic effects. A classic example in oncology is that of imatinib, which inhibits Bcr-Abl kinase with significant degree of specificity (Druker, 2008).

Although small molecules are sometimes known to be protein-protein interaction inhibitors, they rarely exhibit low off-target effects. Secondary structure mimetics have been proposed as effective protein-protein interaction inhibitors (Banerjee et al., 2002; Saraogi and Hamilton, 2008; Walensky et al., 2004). Due to resemblance of the secondary structure mimetics to extant proteins, they may be superior to small molecules in causing lesser undesirable off-target effects. In many situations, a low nanomolar dissociation constant of receptor-drug complex is desirable or even mandatory (Overington et al., 2006). Many protein-protein interactions are weak and attaining high enough affinity for a secondary structure mimetic where the parent protein-protein interaction is weak remains a major challenge. Since many proteins are oligomeric in nature, we propose that properly designed oligomeric secondary structure mimetics (more than one secondary structure mimetic connected by a designed tether) may be a simple way to enhance affinity in such cases.

S100 family of proteins has been implicated in wide variety of tumors, although their precise role is still unclear. Increased levels of S100B are observed in several tumors (Harpio and Einarsson, 2004) and it has been suggested to contribute to tumor progression by interacting and down-regulating p53 and inhibiting its function as a tumor suppressor (Lin et al., 2001; Rustandi et al., 1999; Rustandi et al., 2000; Rustandi et al., 1998b; Wilder et al., 1998). Recent work suggests that other pro-survival pathways may also be regulated by S100B (Brozzi et al., 2009). Thus, inhibition of S100B may simultaneously regulate several key growth regulatory pathways and exert broad anti-tumor effect. Classes of melanomas and gliomas are prime examples of cancers where over-expression of S100B plays a crucial role in cancer development and progression (Markowitz et al., 2005). Thus, there is a real need of agents that block S100B interaction with other proteins.

Keeping in purview the hitherto reported prior art, it may be summarized that most of the therapeutic efforts have been focused on small molecules. There is a recent surge of interest in peptides, although the market is still small. Recent scientific developments have created tremendous opportunity in the therapeutic field. A number of peptides are now in market, but mostly in different phases of trial. However, none are known against melanoma and certainly not with high efficacy. Consequently, there is a dire need to design specific inhibitors of protein-protein interactions that are capable of turning off specific signaling pathways which have an important bearing on the future of therapeutics.

OBJECTS OF THE INVENTION

The main object of the present invention is therefore to provide novel high affinity bivalent helically constrained peptides useful as therapeutics for the treatment of cancers.

Another object of the present invention is to provide an effective therapeutic intervention and method of treatment of several types of tumors in which S100B a calcium binding protein is over-expressed.

Still another object of the present invention is to provide a peptide that completely inhibits melanoma growth without any significant observable toxicity.

Yet another object of the present invention is to provide a pharmaceutical composition for the treatment of cancers comprising the novel bi-helical peptidomimetic.

SUMMARY OF THE INVENTION

Direct inhibition of protein-protein interaction, particularly between weakly interacting proteins, is a major challenge in drug discovery. S100B, a calcium-regulated protein is known to play a crucial role in melanoma and glioma cell proliferation. The present invention relates to a therapeutic peptide against melanoma, glioma and other types of cancers that over-express S100B, a calcium regulated cell progression and differentiation protein. Increased levels of S100B in several tumors contribute to tumor progression by interacting and down regulating p53 and inhibiting its function as a tumor suppressor. Development of high affinity bivalent peptidomimetics is achieved through progressive modifications of p53 target sequence using S100B peptide as a guide. This high affinity bivalent helically constrained peptide against S100B has got the ability to kill cancer cells rapidly with high specificity by exerting anti-proliferative action through simultaneous inhibition of key growth pathways including activation of p53. At moderate intravenous dose, the peptide completely inhibits melanoma growth in a mouse model without any significant observable toxicity.

The present invention provides a high affinity bivalent helically constrained peptide against S100B, which rapidly kills several types of cancer cells that over-express S100B, with high specificity. The molecule exerts anti-proliferative action through simultaneous inhibition of key growth pathways including activation of p53. At moderate intravenous dose, the peptide completely inhibits melanoma growth in a mouse model without any significant observable toxicity. The invention described here provides an effective drug for cancers that over-express S100B.

The bivalent helically constrained peptide of the present invention specifically and effectively blocks S100B and causes rapid apoptosis. Comparison with a well-known p53 activating agent suggests that simultaneous inhibition of key growth pathways is a superior anti-tumor strategy. Also reported is in vivo efficacy of the peptide in a mouse model of melanoma.

Accordingly, the present invention provides a novel high affinity bivalent helically constrained peptide against cancer, wherein the said peptide is represented by SEQ ID No. 10 (SEQ ID No. 4 dimerized with a bridging Lysine (K) in which please note that Ahx corresponds to 6-aminohexanoic acid) and having the following general formula:

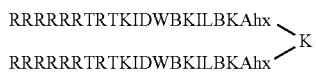

In an embodiment, the present invention provides a pharmaceutical composition comprising a therapeutically effective amount of bi-helical peptidomimetic as an active ingredient optionally along with at least one pharmaceutically acceptable peptide stabilizer and pharmaceutically acceptable excipients, which composition is adapted for the treatment of human cancers in which S100B, a calcium binding protein, is over-expressed resulting in lower level of expression of wild type p53. Human cancers having over-expression of S100B and/or down regulation of p53 include but are not limited to melanoma, glioma, and sarcoma.

In another embodiment, the present invention provides a pharmaceutical composition wherein the bi-helical peptidomimetic comprises of one or more helix stabilizing amino acids and two parallel helices, wherein the polypeptide has enhanced cell penetrability relative to a corresponding unmodified peptide.

In yet another embodiment, the present invention provides the helix-stabilizing amino acids, which stabilize an alpha-helix structure. The bi-helical polypeptide in some embodiment may have cross-linker linking helices in parallel orientation. The bi-helical polypeptide in some embodiment may have branching resulting in parallel orientation of the helices such as branched dimeric aib substituted TRTK (branch dimeric SEQ ID No. 3), having highest affinity towards S100B, enhanced cell penetrability including enhanced energy-dependent transport across a cell membrane, including enhanced endocytosis. The bi-helical polypeptide also comprises a growth retarding, pro-apoptotic polypeptide, such as an alpha-helical domain of Actin capping family protein CapZ or a portion thereof and in some embodiment comprises a S100B binding domain of the protein, p53 or a portion thereof.

In still another embodiment of the present invention the said composition is formulated for oral, parental, subcutaneous, intravenous or intra-articular administration.

In yet another embodiment of the present invention, the said pharmaceutical composition comprises at least one approved chemotherapeutic agent.

In still another embodiment of the present invention, the said composition is adapted for the treatment of human cancers having over-expression of S100B and/or down-regulation of p53 in the dose of approximate 50 mg/kg body weight per day for a period of 1 to 7 days.

In yet another embodiment, the present invention provides a process for the preparation of a medicament for the treatment of S100B over-expressing and/or p53 under-expressing human cancers.

In still another embodiment, the said composition is adapted for inhibiting tumor growth through inhibition of phosphoinositide-3-kinase pathway. The phosphoinositide-3-kinase pathway in some forms initiates the stimulation of some growth factor receptors, e.g. EGFR. This pathway is one of the most crucial pathways for development of many types of cancers activation of which results phosphorylation of GSK-3-beta, Stat-3 and beta-catenin among others. In particular, this invention inhibits this pathway and as a result it reduces the phosphorylation of GSK-3-beta and beta-catenin.

In yet another embodiment, the said composition is adapted for inhibiting tumor growth through inhibition of Src family kinases. In particular, the peptides of this invention inhibit Src-kinase and as a result reduce phosphorylation of Stat-3, resulting in complete inhibition of cell migration.

In still another embodiment, the said composition is adapted for raising the wild-type p53 levels by more than about 50% and 100%. The increase occurs in both cytoplasmic and nuclear compartments.

In yet another embodiment, the said composition is adapted for including rapid apoptosis in a group of cancers having wild-type p53 which is down-regulated by S100B. The rapid apoptosis start in 6 hrs, 2 hrs and 1 hr.

In still another embodiment, the said composition comprises approximate 20% to 80% (w/w) of the bi-helical peptidomimetics, which composition is adapted for the treatment of human cancers having over-expression of S100B and or down-regulation of p53.

In a further embodiment, the present invention provides a method for the treatment of human cancers having over-expression of S100B and/or down-regulation of p53 comprising administering a therapeutically effective amount of the aforesaid composition to a patient in need thereof wherein the said peptidomimetic interacts with S100B.

In another embodiment, the peptidomimetic antagonizes the interaction between S100B and p53.

In still another embodiment, the peptidomimetic antagonizes the interaction between S100B and Src-family kinases.

In yet another embodiment, the present invention provides methods of treatment indicated herein, wherein the peptidomimetic is administered in conjunction with a standard method of care. The standard method of care may, for example be chemotherapy. Alternatively, the standard method of care may be radiation therapy. In a further embodiment, the standard method of care is surgery.

In still another embodiment, the peptidomimetic represented by SEQ ID No. 10 has enhanced cell penetrability relative to the corresponding unmodified peptides represented by branch dimeric SEQ ID No. 3 and branch dimeric SEQ ID No. 5.

BRIEF DESCRIPTION OF THE ACCOMPANYING DRAWING/FIGURES

FIG. 1. (A) Structure of S100B-TRTK peptide complex. The two subunits of S100B shaded differently and the bound peptides are shown as blue ribbons. (B) Design strategy for Aib substitutions. One face of the helix primarily interacts with S100B. The Aib substitutions were made on the opposite face. The substituted residues are marked in blue. The peptide shown represents residues 375-389 of human p53 in the conformation bound to S100B (1DT7) and the substituted residues are 378, 381 and 388. (C) Synthesis strategy for SEQ ID No. 10. The details are given in the description of the invention.

Figure 2C:
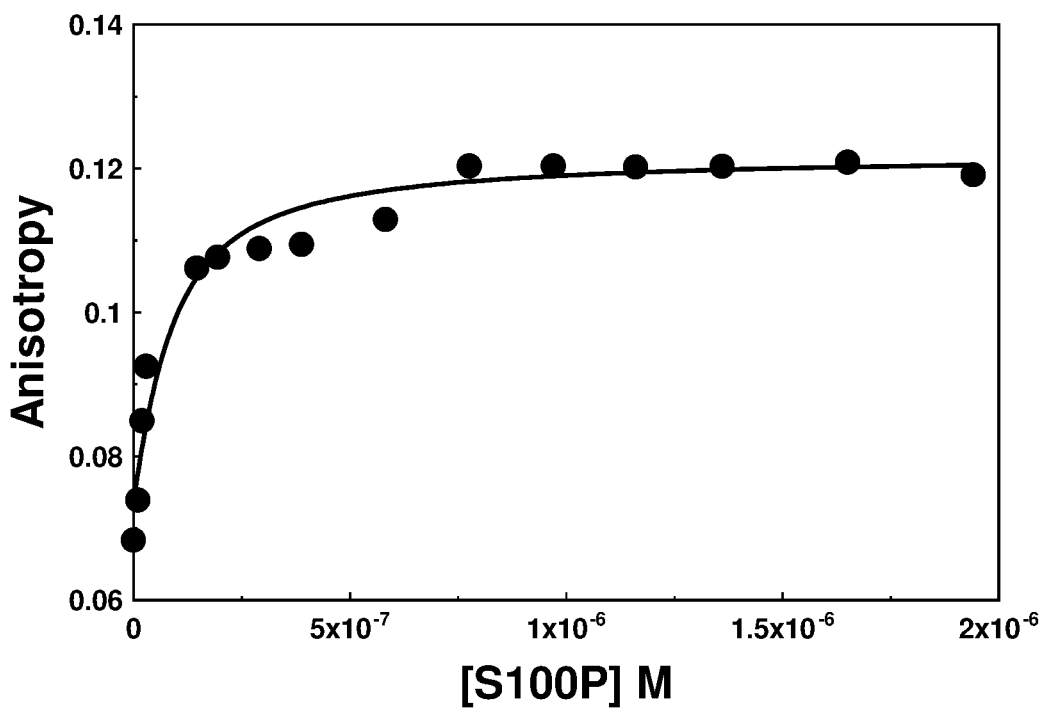
Figure 2D:
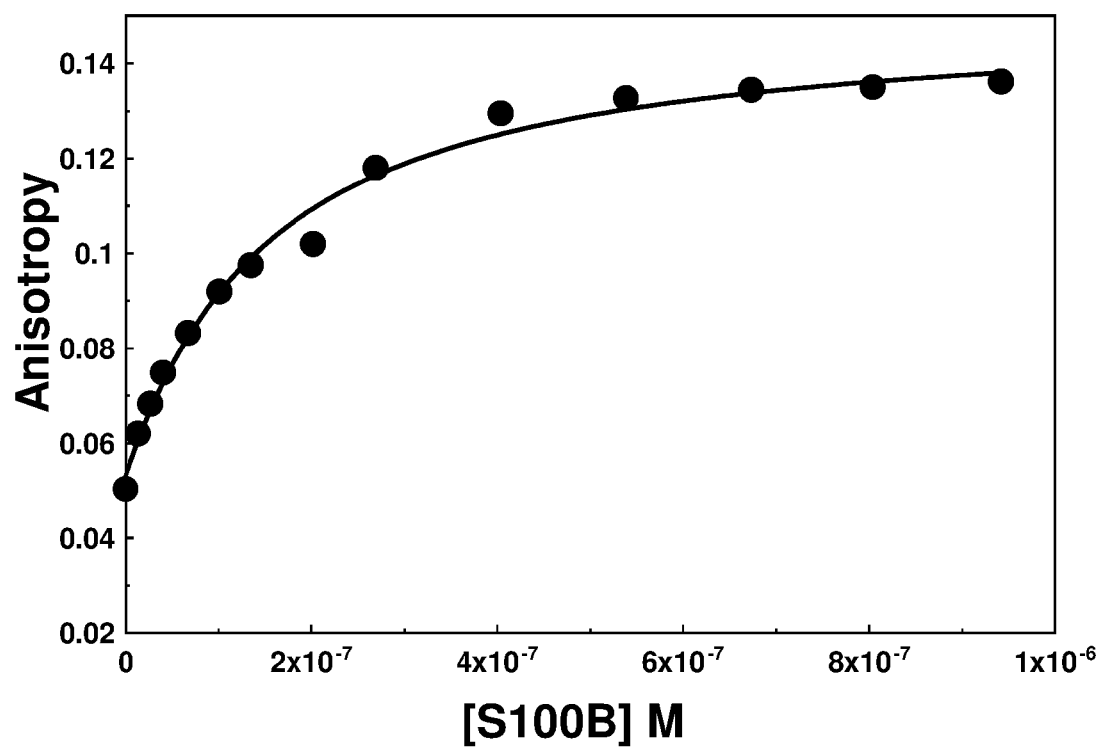

FIG. 2. (A) Table of some representative peptides synthesized which respectively include pM-53 (SEQ ID No. 6), pBN-53 (SEQ ID No. 7), pBDC-53 (SEQ ID No. 8), pBM-TRTK (SEQ ID No. 2), pBDC-TRTK (two SEQ ID No. 2's cross-linked together with BMH), and pBBD-TRTK (SEQ ID No. 11) and their dissociation constants. Binding isotherm of branch dimeric SEQ ID No. 3 (i.e., SEQ ID No. 11) with (B) S-100B and (C) S100P and (D) branch dimeric SEQ ID No. 5 (i.e., SEQ ID No. 12) with S100B. Fluorescein labeled, 5 nM branch dimeric SEQ ID No. 3 (i.e., SEQ ID No. 11) or branch dimeric SEQ ID No. 5 (i.e., SEQ ID No. 12) was titrated with increasing concentrations of S100B or S100P in 50 mM Tris-HCl buffer, pH 7.5, containing 50 mM NaCl and 10 mM $CaCl_2$ at ambient temperatures which was 25±1 degree C. Anisotropy was determined at each point. The each point is averaging of at least three independent experiments. The line is best fit to a single site binding equation given in description of the invention.

Figure 3:
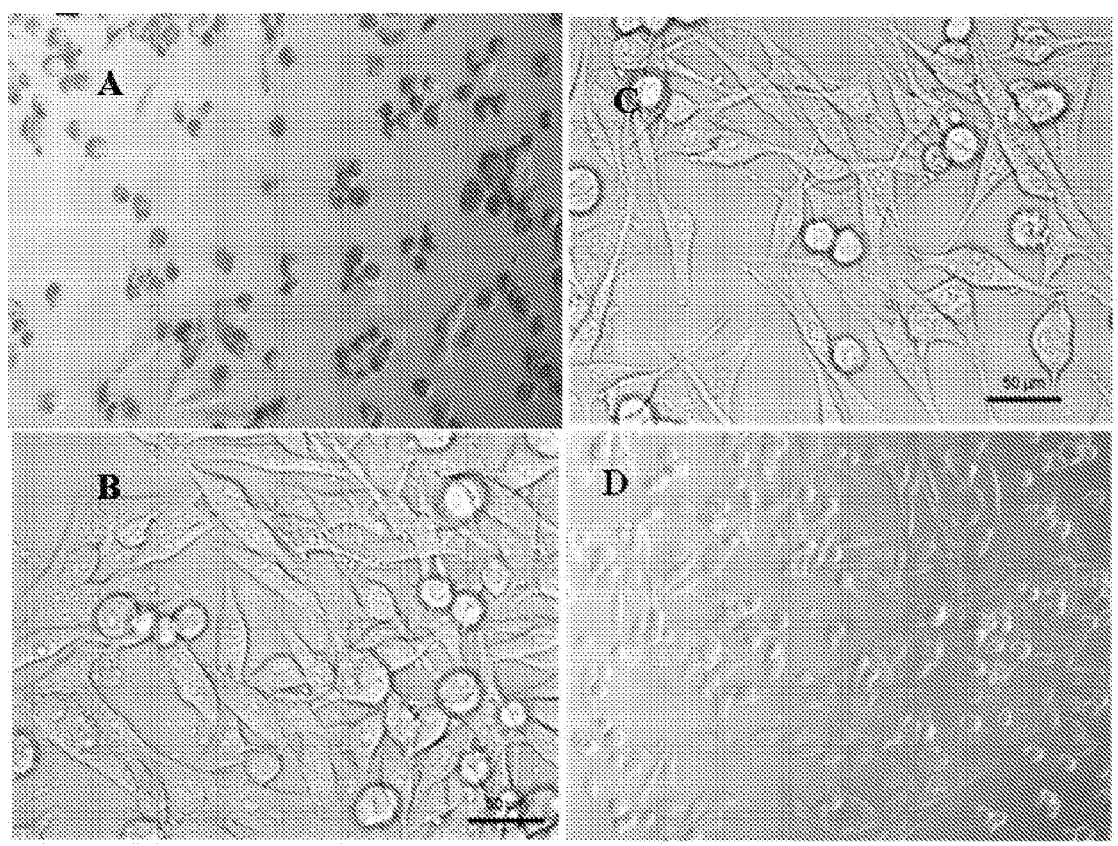

FIG. 3. Phase contrast microscopy of SK-MEL5 cells (A) 2 hrs after treatment with 10 microM SEQ ID No. 10; (B) 18 hrs after treatment with 20 microM branch dimeric SEQ ID No. 5 (i.e., SEQ ID No. 12); (C) 2 hr after treatment with branch dimeric SEQ ID No. 3 (i.e., SEQ ID No. 11) (without the cell penetration tag) and (D) control.

FIG. 4. (A) Assay of cell viability using incorporation of $^3$H-thymidine after treatment with different concentrations of SEQ ID No. 10 for 18 hrs. (B) Flow cytometry of SK-MEL5 cells before and after treatment with 10 microM SEQ ID No. 10 with $DR_6$ tags at two branches, using Annexin V and Propidium Iodide (lower panel) and forward/side scatter (upper panel).

Figure 5:
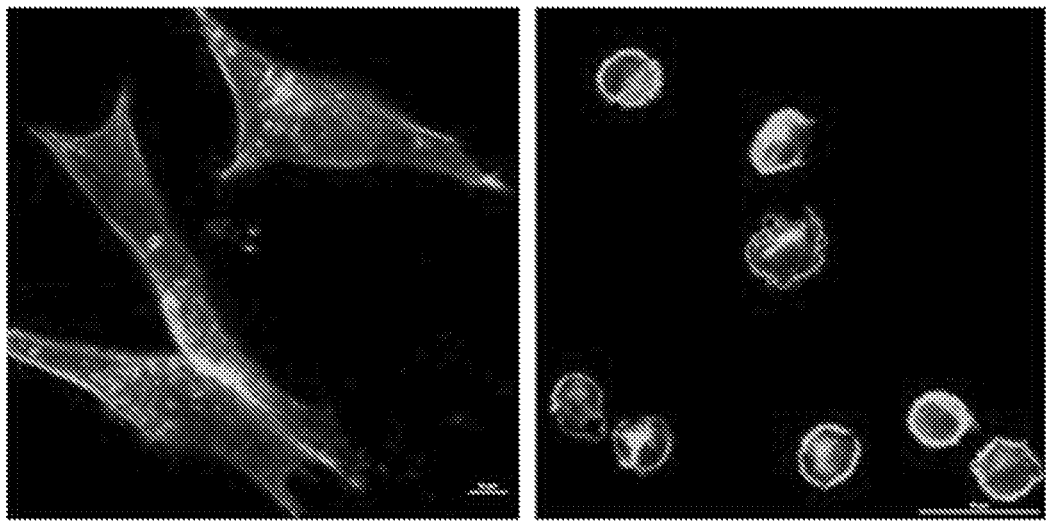
Figure 5:
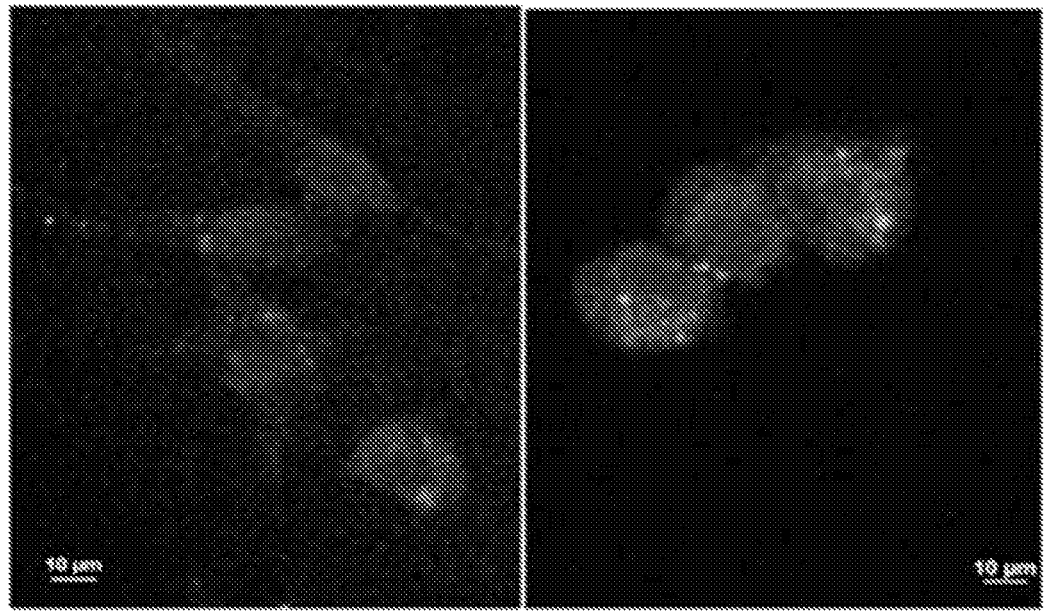

FIG. 5. (A) Confocal Fluorescence microscopic images at 30 minutes of phalloidin (green) and DAPI (blue) stained SK-MELS cells; Left: Untreated, Right: Treated with 10 microM SEQ ID No. 10. (B) Confocal Fluorescence microscopic images of Cytochrome C antibody (green) and DAPI (blue) stained SK-MEL5 cells (Left) Control; (Right) 2 h after treatment with 10 microM SEQ ID No. 10.

Figure 6A:
Figure 6B:
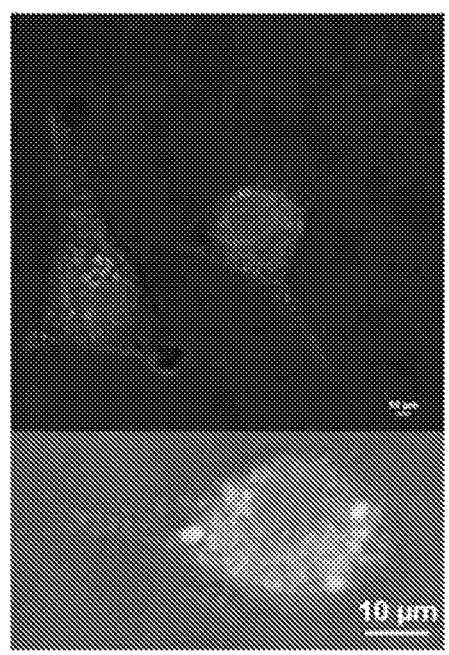

FIG. 6. (A) Phase contrast microscopy of SK-MEL5 cells (Upper panel) 10 microM SEQ ID No. 10 with $DR_6$ tags at two branches (Lower panel), and 10 microM pBBDR-TRTK (i.e., SEQ ID No. 10), pre-treated with 10 microM pifithrin-micro, 1 hr after treatment (Upper panel). (B) Confocal microscopic images of merged p53 (green) and mitotracker (red), Top untreated and bottom, 1 h after treatment with SEQ ID No. 10.

Figure 7:
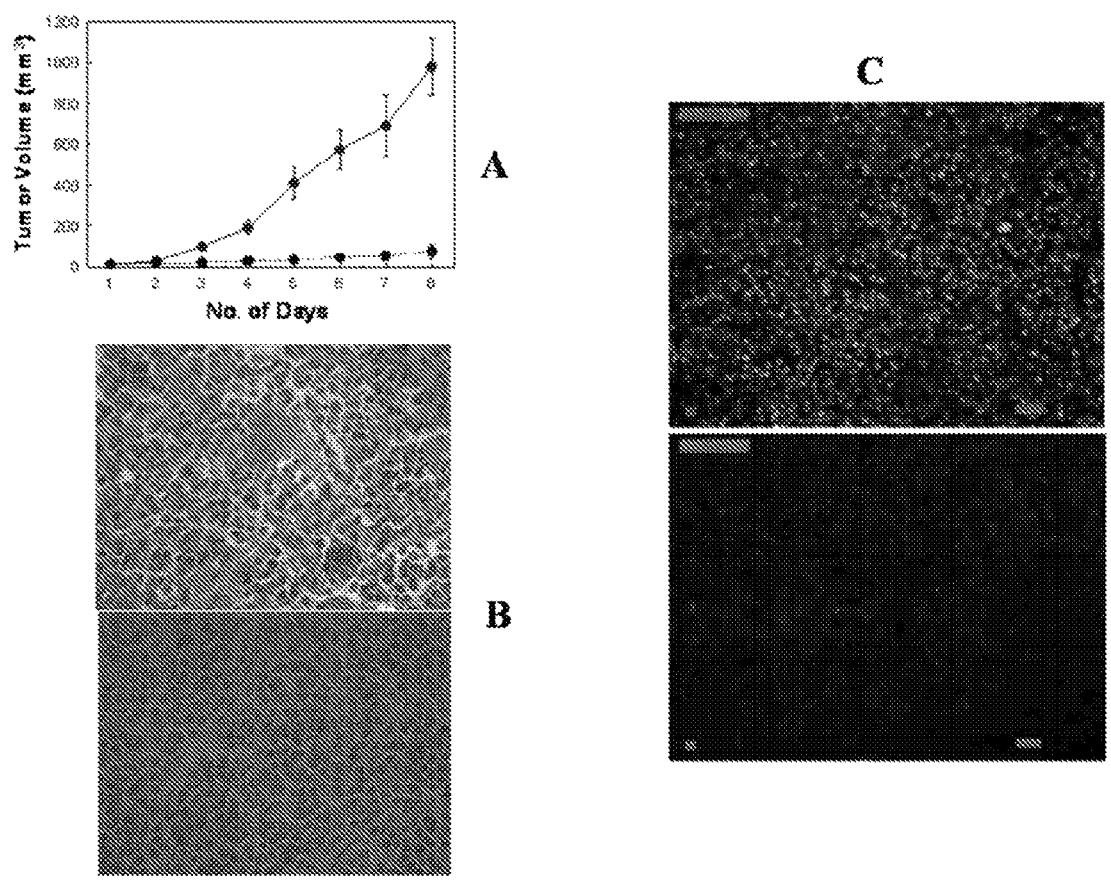

FIG. 7. (A) Kinetics of implanted tumor (B16F10 melanoma cell) growth in syngenic mouse model when treated with 50 mg/kg body wt. i.v. SEQ ID No. 10 (black circles) or vehicle control (blue circles). (B) Histopathology of tumor section after sacrifice of the animals after treatment with SEQ ID No. 10 (upper panel) or vehicle control (lower panel). (C) Antibody staining for PCNA in tumor sections after treatment with SEQ ID No. 10 (lower panel) or vehicle control (upper panel).

FIG. 8. Efficacy of the peptidomimetic (SEQ ID No. 10) in a C57BL/6J melanoma xenograft model as measured by reduced tumor burden in treated animals.

FIG. 9. p53 staining of the tumor sections after treatment with 1 dose of 50 mg/Kg body weight of SEQ ID No. 10 (left panel) and vehicle control (right panel).

FIGS. 10 and 11. Flow charts illustrating the process/steps of development of high affinity bivalent peptidomimetics achieved through progressive modifications of p53 (i.e., SEQ ID No. 6) target sequence using S100B peptide as a guide.

LIST OF ABBREVIATIONS USED

TABLE 1

Chart of Amino Acid with their structure and abbreviation

| Sl. No | Name of Amino Acid | Abbreviation used | Structure |
|---|---|---|---|
| 01 | Threonine (Thr) | T | 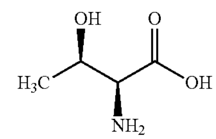 |
| 02 | Arginine (Arg) | R | 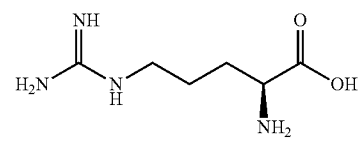 [SMILES: N=C(N)NCCC[C@H](N)C(=O)O] |
| 03 | Lysine (Lys) | K | 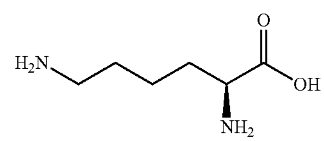 |
| 04 | Isoleucine (Ile) | I | 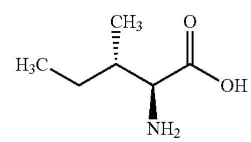 |
| 05 | Leucine (Leu) | L | 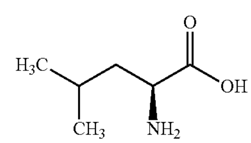 |
| 06 | Aminoisobutyric Acid(Aib) | B | 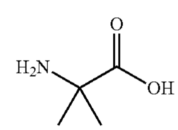 |
| 07 | Aspartic Acid (Asp) | D | 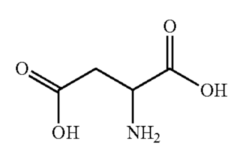 |
| 08 | Tryptophan (Trp) | W | 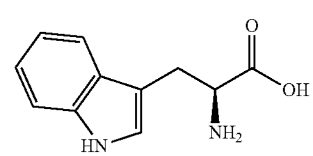 [SMILES: N[C@@H](Cc1c[nH]c2ccccc12)C(=O)O] |
| 09 | Aminohexanoic acid (Ahx) | Ahx | 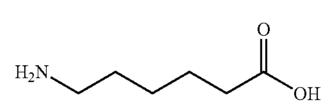 |

TABLE 1-continued

Chart of Amino Acid with their structure and abbreviation

| Sl. No | Name of Amino Acid | Abbreviation used | Structure |
|---|---|---|---|
| 10 | Glycine (Gly) | G | 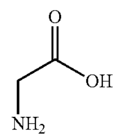 |
| 11 | Cysteine (Cys) | C | 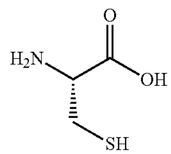 |
| 12 | Phenylalanine (Phe) | F | 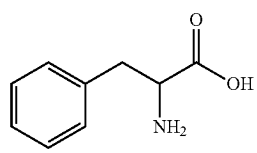 [SMILES: NC(Cc1ccccc1)C(=O)O] |
| 13 | Methionine (Met) | M | 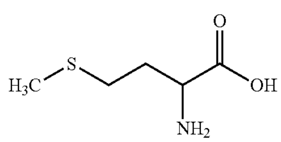 |
| | Histidine (His) | H | |
| | Serine (Ser) | S | |
| | Glutamine (Gln) | Q | |
| | Arginine (Arg) | R | |

TABLE 2

Details of some of the synthesized peptides

| No. | Name of the peptide/peptidomimetic and corresponding SEQ ID No. | What it signifies/means/pertains to | The exact sequence in terms of one letter amino acid codes |
|---|---|---|---|
| 1. | P53 SEQ ID No. 6 | Wild type P53 peptide | QSTSRHKKLMFKTEG |
| 2. | pBM53 SEQ ID No. 7 | P53 Aib substituted monomer peptide | QSTBRHBKLMFKTBG |
| 3. | pBDC-53 two SEQ ID No. 8 cross linked together | GCGG Modified pBM53 dimerised with a properly designed crosslinker (i.e., BMH crosslinker) | GCGGGBTKFMLKBHRBTSQ<br><br>QSTBRHBKLMFKTBGGGCG |
| 4. | pBM-TRTK SEQ ID No. 4 | Aib substitued TRTK monomer peptide | TRTKIDWBKILBGGGCG |
| 5. | pBDC-TRTK two SEQ ID No. 2 cross linked together | pBM-TRTK dimerised with a properly designed crosslinker [Wild type TRTK peptides bind to two subunits of S100B in a head-to-head fashion. In order to make a dimeric peptide a linker was designed which spans the distance between two C-termini of the peptides. Modeling indicated that addition of GGGCG at the C-terminus along with BMH cross-linker spans this distance.] | GCGGGBLIKBWDIRTRI<br><br>TRIKIDWBKILBGGGCG |

TABLE 2-continued

Details of some of the synthesized peptides

| No. | Name of the peptide/ peptidomimetic and corresponding SEQ ID No. | What it signifies/means/ pertains to | The exact sequence in terms of one letter amino acid codes |
|---|---|---|---|
| 6. | pBBD-TRTK SEQ ID No. 11 (SEQ ID No. 3 dimerized with bridging lysine) | pBM-TRTK branched dimerised with a proper crosslinker | TRTKIDWBKILBKAhx\<br>　　　　　　　　　　＼<br>　　　　　　　　　　　K<br>　　　　　　　　　　／<br>TRTKIDWBKILBKAhx |
| 7. | pBBD-TRTK-AA SEQ ID No. 12 (SEQ ID No. 5 dimerized with bridging lysine)) | pBM-TRTK double mutant branched dimer mutated at (Ile-5 and Trp-7) | TRTKADABKILBKAhx\<br>　　　　　　　　　　＼<br>　　　　　　　　　　　K<br>　　　　　　　　　　／<br>TRTKADABKILBKAhx |
| 8. | pBBDR-TRTK SEQ ID No. 10 | pBM-TRTK branched dimerised with a properly designed crosslinker and tagged with hexa-arginine | RRRRRRTRTKIDWBKILBKAhx\<br>　　　　　　　　　　　　　　＼<br>　　　　　　　　　　　　　　　K<br>　　　　　　　　　　　　　　／<br>RRRRRRTRTKIDWBKILBKAhx |
| 9. | pBDCR-TRTK two SEQ ID No. 13 crosslinked together | pBM-TRTK dimerised with a properly designed crosslinker (i.e., BMH crosslinker) and tagged with hexa-arginine | GCGGGBTKFMLKBHRBTSQ<br>　　　　　　＼<br>　　　　　　　N～～～N<br>　　　　　　　　　　　　＼<br>　　　　　　　　　QSTBRHBKLMFKTBGGGCG |

| List of sequences used in the invention | |
|---|---|
| Sequence | Sequence ID No. |
| TRTKIDWNKILS | SEQ ID No. 1 |
| TRTKIDWBKILBGGGCG | SEQ ID No. 2 |
| TRTKIDWBKILBKAhx | SEQ ID No. 3 |
| RRRRRRTRTKIDWBKILBKAhx | SEQ ID No. 4 |
| TRTKADABKILBKAhx | SEQ ID No. 5 |
| QSTSRHKKLMFKTEG | SEQ ID No. 6 |
| QSTBRHBKLMFKTBG | SEQ ID No. 7 |
| QSTBRHBKLMFKTBGGGCG | SEQ ID No. 8 |
| RRRRRRQSTBRHBKLMFKTBGGGCG | SEQ ID No. 9 |

DETAILED DESCRIPTION OF THE INVENTION

Two target sequences of S100B [TRTK (12 a.a.) and 375-389 of p53 are helical when bound to the receptor (FIG. 1(A)]. Small peptides generally do not have definite structures in solution and hence binding to the receptor involves sacrifice of entropy as the structure becomes more ordered upon binding. A constrained helical peptide may have higher affinity due to less sacrifice of entropy upon binding and enhanced in vivo stability as was shown for stapled monomeric helix mimetics (Moellering et al., 2009). We have chosen substitution of helicogenic alpha-amino-isobutyric acid (Aib) substitution as an alternative due to its simple synthesis methodology and possibly better scaling up potential for bivalent molecules (Vijayalakshmi et al., 2000). Using the structures of the S100B-peptide as a guide, we replaced only those residues in the target peptides that are not interacting with S100B, but are still part of the target sequence (Banerjee et al., 2002) (FIG. 1(B)). Wild type TRTK peptides bind to two subunits of S100B in a head-to-head fashion. In order to make a dimeric peptide a linker was designed which spans the distance between two C-termini of the peptides. Modeling indicated that addition of GGGCG at the C-terminus along with BMH cross-linker spanned this distance.

Binding affinity of aib substituted p53 (SEQ ID No. 7) (and all other peptides) was estimated by fluorescence anisotropy using N-terminal fluorescein labeled peptides. SEQ ID No. 7 binds to S100B somewhat stronger than the unmodified peptide but the dissociation constant is still in the micromolar range. Since S100B is a dimer, one possible way to enhance the binding is to synthesize a bivalent molecule, which can simultaneously bind to two subunits. SEQ ID No. 7 was dimerized with a properly designed cross-linker through inserted cysteine residues (SEQ ID No. 8). The C-terminal side of the two peptides (bound to two different subunits) comes fairly close and is separated by shallow groove allowing a cross-linker to fit. The length of the cross-linker was chosen such that it spans the separation between the two cysteine residues in the predicted structure. The dimerization leads to approximately 15 fold increases in affinity. This suggests that proper structure guided dimerization is a tool for enhancing affinity of the therapeutic peptides. SEQ ID No. 3 on the other hand binds to S100B with a $K_d$ of about 300 nM, significantly tighter than SEQ ID No. 6 and SEQ ID No. 7. When cross-linked through suitably placed cysteine residues (SEQ ID No. 2), the dimeric peptide showed approximately an order of magnitude tighter binding. However, the yield of cysteine cross-linked reaction is generally low and hence we have attempted to create a bivalent peptide by synthesizing a branched peptide on solid-phase (branch dimeric SEQ ID No.

3) (FIG. 1 (C)). The synthesis of the branched peptide in solid phase gave much superior yield and even higher affinity, thus making scale-up possible for in vivo work.

Binding data of the several of these peptides are shown in FIG. 2 (A) and some of the corresponding binding isotherms are shown FIG. 2(B-D). Of the two branched mimetics based on TRTK target sequence, branch dimeric SEQ ID No. 3, has the highest affinity towards S100B with a dissociation constant of 7.7±3.5 nM. The selectivity of the bivalent peptide, branch dimeric SEQ ID No. 3 was demonstrated by approximately 7-fold weaker binding of branch dimeric SEQ ID No. 3 to S100P, the closest paralog of S100B (Marenholz et al., 2004). Also synthesized was a mutant branched peptide (SEQ ID No. 12 which is a lysine branch dimeric form of SEQ ID No. 5) bearing two mutations in the interacting residues. This peptide binds to S100B with a $K_d$ of 135±18.5 nM. This peptide will be used as a control in the cellular experiments to be described later.

The effect of all the synthesized peptides on several melanoma cell lines which are known to over-express S100B was investigated. The SEQ ID No. 10 (lysine branch dimeric SEQ ID No. 3 with six D-arginine residues as cell penetrating peptide in each branch at the N-terminal end) induces apoptosis at lowest concentrations among all the peptides and in all melanoma and glioma cell lines tested; henceforth results will be largely described using this molecule and pre-dominantly on SK-MEL-5 cells, unless specifically mentioned otherwise. FIG. 3 shows the change of appearance of SK-Mel-5 at 10 µM concentration of the SEQ ID No. 10. The cells change shape within a few minutes after addition of SEQ ID No. 10 and shows typical apoptotic changes, such as blebbing within 1 hr. SEQ ID No. 10 enters the cell within a short period of time.

Specificity of the peptide was tested by using the previously described double mutant peptide lysine branch dimeric SEQ ID No. 5 (i.e., SEQ ID No. 12), which binds to S100B with about 20 fold lower affinities. This peptide, which is otherwise identical to SEQ ID No. 10, does not show any apoptotic effect at 20 microM, even at 18 hrs. The lysine branch dimeric SEQ ID No. 3 (i.e., SEQ ID No. 11), which lacks the cell penetration tag, shows no apoptotic effect on SK-MEL5 cell line, suggesting that the effect of SEQ ID No. 10 is due to specific inhibition of intracellular S100B.

The effect of SEQ ID No. 10 on viability was also measured by $^3$H thymidine uptake (FIG. 4 (A)). The measured $IC_{50}$ by this method was less than 2 µM. The apoptosis of SK-Mel5 cells was quantitated using flow cytometry. 49% of cells were determined to be apoptotic and 11% necrotic at 2 hrs using annexin V stain. Corresponding figures for 6 hrs were 57% and 14%, respectively (FIG. 4(B)). From the results presented here and analysis of growth promoting pathways described later-S100B appears to be a generalized growth promoter, when over-expressed.

Treatment with SEQ ID No. 10 causes cells to quickly become round. Attempts were made to find out whether this involved reorganization of actin cytoskeleton. Phalloidin staining was used to observe the actin fibers (FIG. 5(A)). The cells looked elongated in the beginning with distinct fibers of actin visible upon phalloidin staining. Upon treatment with SEQ ID No. 10, the cells changed shape within 30 minutes and the actin fibers reorganized. The massive reorganization of actin fibers was accompanied by cell shape change followed by signs of typical apoptotic changes such as blebbing. Apoptotic nature of cell death was confirmed by release of cytochrome C from mitochondria (FIG. 5(B)).

Given the rapidity of apoptosis initiation, the examination of the recently reported direct mitochondrial translocation pathway was also done by the method if Vaseva and Moll, 2009. It has been reported that a small molecule pifithrin-micro blocks this pathway without affecting the canonical transcription-dependent pathway of p53 initiated apoptosis and a close analog, pifithrin-α blocks the canonical pathway without affecting the direct mitochondrial pathway (Strom et al., 2006). In these experiments, SEQ ID No. 2 with $DR_6$ tags at two branches was used which was nearly as potent as SEQ ID No. 10 FIG. 6 (A) shows the effect of pifithrin-µ on the apoptosis induced by SEQ ID No. 2 with $DR_6$ tags at two branches. Interestingly in the presence of pifithrin-µ the cells change shape very quickly, but blebbings are not seen, whereas in its absence both shape change and blebbings are seen, indicating initiation of apoptosis. The direct translocation of p53 to mitochondria was also verified by confocal microscopy (FIG. 6(B)). Thus, early shape change of the cells involving actin cytoskeleton may be a p53 independent effect, hypothetically as a result of direct role of S100B on actin cytoskeleton.

The effect of SEQ ID No. 10 was tested in a syngenic mouse model of melanoma. SEQ ID No. 10 was found to be non-lethal and showed no demonstrable toxicity upto a tested concentration of 50 mg/Kg body weight. Histopathology of some key target organs after 8 days of treatment was normal, indicating no significant toxicity. At this dose level the tumor growth was completely inhibited up to 8 days (maximum tested) (FIG. 7 (A)). Histopathology of tumor sections, when compared to untreated tumors, showed large areas devoid of live cells (FIG. 7(B)). Immuno-histochemistry of growth marker PCNA indicates complete loss of this antigen in the residual tumor mass upon treatment, indicating complete loss of proliferating cells (FIG. 7(C)).

The significance of this invention relates to the possibility that peptides may be better therapeutic molecules than small molecules for certain class of targets. The small molecules today are the mainstay of drug discovery research and as tools of chemical genetics. However, they have deficiency as protein-protein interaction inhibitors, a new class of drug targets. Peptides are thought to have superior specificity as protein-protein interaction inhibitors, but suffer from disadvantages. Constrained secondary structure mimetics are potential drugs but may not have high affinity when the parent protein-protein interactions are weak. In this study, we have shown that designed construction of bivalent helix mimetic against a dimeric protein, S100B, is an effective way to increase the affinity. The specificity of the bivalent mimetic is high as it is able to discriminate against a close paralog. When this molecule is directed inside the cell by attachment to a cell penetrating peptide, it specifically induces rapid apoptosis in cancer cells that over-express S100B. The invented molecule is shown to be effective against implanted melanoma in a mouse model of tumor.

EXAMPLES

The following examples are given by way of illustration and therefore should not be construed to limit the scope of the present invention.

Example 1

Synthesis and Purification of Bivalent Helically Branched Peptide

The bivalent helically branched peptide of TRTK-12, from the actin capping protein CapZ of residues 265-276: TRTKIDWNKILS (i.e., SEQ ID No. 1) (Weber. et, al 2002) with Aib substituted at N8 and S12 was synthesized on 0.3 mmol scale by using a solid-phase peptide synthesis strategy using 9-fluorenylmethoxy carbonyl chemistry, amino acid/HCTU/DIPEA in the ratio 1:1:2, dry mixed solvent DMF/NMP in the ratio 3:2 and rink amide pega resin (Novabiochem) in (PS3, Protein Technologies Inc.). Capping of the undesired coupled product and the desired uncoupled amino acid was performed essentially after each coupling by using acetic anhydride and lutidine as base (200 μM acetic anhydride, 300 μl lutidine mixed with 5 ml DMF and coupled for 10 minutes in each capping procedure). First fmoc-lys(fmoc)-OH is attached with the resin mentioned above then both the 9-fluorenyl-methoxy carbonyl is cleaved using 20% piperidene in DMF then fmoc ε-aminohexanoic acid is attached with it followed by fmoc-lys(boc)-OH and finally Aib substituted 12 mer TRTK peptide is attached with it using same protocol. Cleavage of the peptide from rink amide pega resin (Novabiochem) and removal of all the side chain-protecting groups were achieved in 87.5% trifluoroacetic acid solution containing 2.5% TIS, 5% EDT and 5% phenol.

Purification of the Bivalent Helically Branched Peptide

The crude peptide was purified by reversed-phase high performance liquid chromatography (Waters Associates) with a water reversed-phase C18 column (micro Bondapac) with linear gradients of Water/acetonitrile containing 0.1% trifluoroacetic acid. Peptide masses and purity were checked by positive ion mode electrospray ionization mass spectrometry (Waters Inc.) and MALDI-TOF mass spectrometry.

Peptide Labelling

The bivalent helically branched peptide was labeled with 5(6)-carboxy Fluorescein in solid phase at both the N-termini. Dry resin bound N-terminal deprotected peptide (3 μmol) was taken in a 2 ml polypropylene syringe and reacted with 10 times molar excess of 5(6)-carboxy Fluorescein and HOBT (1:1) in DMF mixed with 2-4 μl of DIPC. The reaction was incubated for 4-6 hours in dark at 25° C. After completion of the reaction, the resin was washed thoroughly with 20% piperidene solution in DMF until the washed solution becomes colorless. Resin was then washed consecutively with DMF and finally with diethyl ether for five times and then dried under nitrogen atmosphere. After labeling, peptide was cleaved using the same protocol as mentioned above and purified by HPLC, which was monitored at 490 nm wave length and Masses were checked by Mass Spectrometry.

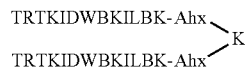

Structure of the bivalent helically constrained peptide pBBD-TRTK. (The corresponding Amino Acid structure and their abbreviation is given in table 1)

Since S100B is a dimer, one possible way to enhance the binding is to synthesize a bivalent molecule, which can simultaneously bind to two subunits. SEQ ID No. 7 was dimerized with a properly designed cross-linker through inserted cysteine residues (SEQ ID No. 8).

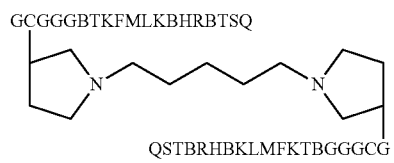

Structure of the peptide PBDC-53 with the corresponding Amino Acid structure. The corresponding Amino Acid structure and their abbreviation is given in table no. 2

The cross linker used was BMH (1,6-bismalimeido hexane) which has the carbon-carbon covalent bond distance near about 16.5° A and attached with the sulphur of cysteine of both the limbs of the peptide. The structure of BMH is as follows

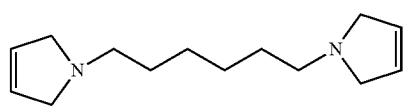

Structure of the cross linker 1,6-Bismaleimido hexane

Example 2

Animal Studies: The Invented Molecule was Shown to be Effective Against Implanted Melanoma in a Mouse Model of Tumor Experiments were carried out under protocols approved by the Institutional Animal Ethics Committee and institutional guidelines for the proper use of animals in research were followed. National guidelines had been followed. C57BL/6J female mice (mean initial weight, 20 g) were kept in one mice in one cage at 19° C. to 23° C. with a 12 hour light/12 hour dark cycle. They had free access to water and food. To generate tumor, $1\times10^6$ B16F10 cells were mixed with Matrigel (BD bioscience) and inoculated S.C. in the right flank of 6 week-old mice. Tumors (typically 2 mm in diameter) were palpable 5 days after subcutaneous injection. Peptide treatments (50 mg/kg body weight) were administered by intravenous tail vein injection on the day tumors became apparent (day 0) and then days 1, 2, 3, 4, 5, 6 and 7. Control mice were treated only with saline vehicle. Mice were weighted, and tumor volumes were calculated with the following formula: $\pi/6\times$larger diameter$\times$(smaller diameter)$^2$. The tumor sections after only one treatment of SEQ ID No. 10 was stained for p53, which exhibited significant enhancement in contrast to a control tumor section (FIG. 8).

Example 3

Branched Peptides Synthesis and Purification

The branched peptide SEQ ID No. 10 having the sequence $^DR_6$ TRTKIDWBKILBKAhxKAhxKBLIKBWDIKTRT-$^DR_6$] and its mutant peptide lysine branch dimeric SEQ ID No. 5 (i.e., SEQ ID No. 12) having the sequence TRTKAD-ABKILBKAhxKAhxKBLIKBADAKTRT-(I5A,W7A)] along with their hexa-arginine tagged variety were synthesized on a PS3 Protein Technologies peptide synthesizer at 0.3 mmol scale by using a solid-phase peptide synthesis strategy using 9-fluorenylmethoxy carbonyl chemistry and Rink amide PEGA resin. The branching of the peptide starts from α-NH$_2$ as well as δ-NH$_2$ group of (fmoc)Lys(Fmoc) and the linker ε-Aminohexanoic acid to maintain the distance 30 A. Cleavage of the peptides from Rink amide PEGA resin and removal of all side chain-protecting groups were achieved in 87.5% trifluoroacetic acid 2.3% water, 2.5% 1,2-ethanedithiol and 2.5% triisopropylsilan solution 2.5% water. The crude peptides were purified by reversed-phase high-performance liquid chromatography (Waters Associates) with a C$_{18}$ column (Hypersil gold, Thermo Fisher) with linear gradients of water/acetonitrile containing 0.1% trifluoroacetic acid. Peptides masses and purity (>95%) were checked by ESI (Waters Inc.) and MALDI.

Peptides Labeling

The branched peptides and its mutant (I5, W7) along with their hexa-arginine tagged variety were labeled with 5,6-carboxy fluorescein in solid phase and cleaved as unlabeled peptides and purified by HPLC.

Testing of cytotoxic activity of bi-valent helically constrained peptides on cancer cell lines of different origin which are known to over-express S100B and peripheral blood mononuclear cells of normal individuals was carried out in vitro. The in vitro studies indicated that the bi-valent helically constrained peptides show preferential cytotoxicity towards cancer cell lines of different origin leaving normal human peripheral blood mononuclear cells unaffected. In vivo efficacy of bi-valent helically constrained peptide was evaluated on tumors of syngenic mouse model of melanoma. It was observed that the peptides when administered intravenously were effective in vivo in syngenic mouse by destroying the tumor. Treatment with the prepared peptides caused cells to quickly become round. The massive reorganization of actin fibers was accompanied by cell shape change followed by signs of typical apoptotic changes such as blebbing.

It was conclude that the bivalent helically constrained peptides described above induced the direct translocation of p53 to mitochondria, which is responsible for cancer cell killing.

The best peptide/peptidomimetic having therapeutic significance was observed to be SEQ ID No. 10 (SEQ ID No. 3 branched dimerised with a proper crosslinker and tagged with hexa-arginine) represented by SEQ ID No. 10 and having the following general formula:

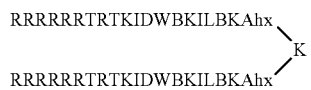

Advantages

The present disclosure provides an effective therapeutic intervention and treatment of several types of tumor in which S100B a calcium binding protein is over-expressed.

These proliferative disorders include Melanoma, glioma and other types of cancers in which the wild-type p53 level is lowered.

The invention presented here demonstrated that certain designed peptide exhibit high efficacy of tumor cell killing with high degree of specificity in above mentioned cancers.

REFERENCES

Banerjee, R., Basu, G., Chene, P., and Roy, S. (2002). Aib-based peptide backbone as scaffolds for helical peptide mimics. J Pept Res 60, 88-94.

Bartkova, J., Rezaei, N., Liontos, M., Karakaidos, P., Kletsas, D., Issaeva, N., Vassiliou, L., Kolettas, E., Niforou, K., and Zoumpourlis, V. (2006). Oncogene-induced senescence is part of the tumorigenesis barrier imposed by DNA damage checkpoints. Nature 444, 633-637.

Brozzi, F., Arcuri, C., Giambanco, I., and Donato, R. (2009). S100B Protein Regulates Astrocyte Shape and Migration via Interaction with Src Kinase: IMPLICATIONS FOR ASTROCYTE DEVELOPMENT, ACTIVATION, AND TUMOR GROWTH. J Biol Chem 284, 8797-8811.

Chattopadhyay, D., Ghosh, M., Mal, A., and Harter, M. (2001). Inactivation of p21 by E1A leads to the induction of apoptosis in DNA-damaged cells. Journal of Virology 75, 9844.

Drohat, A., Baldisseri, D., Rustandi, R., and Weber, D. (1998). Solution Structure of Calcium-Bound Rat S100B ([beta][beta]) As Determined by Nuclear Magnetic Resonance Spectroscopy†, ‡. Biochemistry 37, 2729-2740.

Druker, B. (2008). Translation of the Philadelphia chromosome into therapy for CML. Blood 112, 4808-4817.

Greenman, C., Stephens, P., Smith, R., Dalgliesh, G., Hunter, C., Bignell, G., Davies, H., Teague, J., Butler, A., and Stevens, C. (2007). Patterns of somatic mutation in human cancer genomes. Nature 446, 153-158.

Harpio, R., and Einarsson, R. (2004). S100 proteins as cancer biomarkers with focus on S100B in malignant melanoma. Clin Biochem 37, 512-518.

Jirina Bartkova, Z. (2005). DNA damage response as a candidate anti-cancer barrier in early human tumorigenesis. Nature 434, 864-870.

Komori, H., Ichikawa, S., Hirabayashi, Y., and Ito, M. (1999). Regulation of intracellular ceramide content in B16 melanoma cells. Journal of Biological Chemistry 274, 8981.

Lin, J., Blake, M., Tang, C., Zimmer, D., Rustandi, R. R., Weber, D. J., and Carrier, F. (2001). Inhibition of p53 transcriptional activity by the S100B calcium-binding protein. J Biol Chem 276, 35037-35041.

Lin, J., Yang, Q., Wilder, P., Carrier, F., and Weber, D. (2010). The calcium-binding protein S100B down-regulates p53 and apoptosis in malignant melanoma. Journal of Biological Chemistry.

Lin, J., Yang, Q., Yan, Z., Markowitz, J., Wilder, P. T., Carrier, F., and Weber, D. J. (2004). Inhibiting S100B restores p53 levels in primary malignant melanoma cancer cells. J Biol Chem 279, 34071-34077.

Lyu, P., Sherman, J., Chen, A., and Kallenbach, N. (1991). Alpha-helix stabilization by natural and unnatural amino acids with alkyl side chains. Proceedings of the National Academy of Sciences of the United States of America 88, 5317.

Marenholz, I., Heizmann, C., and Fritz, G. (2004). S100 proteins in mouse and man: from evolution to function and pathology (including an update of the nomenclature). Biochemical and biophysical research communications 322, 1111-1122.

Markowitz, J., Mackerell, A. D., Jr., Carrier, F., Charpentier, T. H., and Weber, D. J. (2005). Design of Inhibitors for S100B. Curr Top Med Chem 5, 1093-1108.

Mauro, M. J. (2006). Defining and managing imatinib resistance. Hematology Am Soc Hematol Educ Program, 219-225.

Moellering, R. E., Cornejo, M., Davis, T. N., Del Bianco, C., Aster, J. C., Blacklow, S. C., Kung, A. L., Gilliland, D. G., Verdine, G. L., and Bradner, J. E. (2009). Direct inhibition of the NOTCH transcription factor complex. Nature 462, 182-188.

Overington, J. P., Al-Lazikani, B., and Hopkins, A. (2006). How many drug targets are there? Nat Rev Drug Disc 5, 993-996.

Rust, R., Baldisseri, D., and Weber, D. (2000). Structure of the negative regulatory domain of p53 bound to S100B ( ). Nature Structural & Molecular Biology 7, 570-574.

Rustandi, R., Drohat, A., Baldisseri, D., Wilder, P., and Weber, D. (1998a). The Ca2+-Dependent Interaction of S100B ([beta][beta]) with a Peptide Derived from p53†. Biochemistry 37, 1951-1960.

Rustandi, R. R., Baldisseri, D. M., Drohat, A. C., and Weber, D. J. (1999). Structural changes in the C-terminus of Ca2+-bound rat S100B (beta beta) upon binding to a peptide derived from the C-terminal regulatory domain of p53. Protein Sci 8, 1743-1751.

Rustandi, R. R., Baldisseri, D. M., and Weber, D. J. (2000). Structure of the negative regulatory domain of p53 bound to S100B(betabeta). Nat Struct Biol 7, 570-574.

Rustandi, R. R., Drohat, A. C., Baldisseri, D. M., Wilder, P. T., and Weber, D. J. (1998b). The Ca(2+)-dependent interaction of S100B(beta beta) with a peptide derived from p53. Biochemistry 37, 1951-1960.

Saraogi, I., and Hamilton, A. D. (2008). alpha-Helix mimetics as inhibitors of protein-protein interactions. Biochem Soc Trans 36, 1414-1417.

Senatus, P., Li, Y., Mandigo, C., Nichols, G., Moise, G., Mao, Y., Brown, M., Anderson, R., Parsa, A., and Brandt-Rauf, P. (2006). Restoration of p53 function for selective Fas-mediated apoptosis in human and rat glioma cells in vitro and in vivo by a p53 COOH-terminal peptide. Molecular cancer therapeutics 5, 20.

Shangary, S., and Wang, S. (2009). Small-molecule inhibitors of the MDM2-p53 protein-protein interaction to reactivate p53 function: a novel approach for cancer therapy. Annu Rev Pharmacol Toxicol 49, 223-241.

Sreerama, N., and Woody, R. (2000). Estimation of protein secondary structure from circular dichroism spectra: comparison of CONTIN, SELCON, and CDSSTR methods with an expanded reference set. Analytical biochemistry 287, 252-260.

Strom, E., Sathe, S., Komarov, P. G., Chernova, O. B., Pavlovska, I., Shyshynova, I., Bosykh, D. A., Burdelya, L. G., Macklis, R. M., Skaliter, R., et al. (2006). Small-molecule inhibitor of p53 binding to mitochondria protects mice from gamma radiation. Nat Chem Biol 2, 474-479.

Van Maerken, T., Ferdinande, L., Taildeman, J., Lambertz, I., Yigit, N., Vercruysse, L., Rihani, A., Michaelis, M., Cinatl Jr, J., and Cuvelier, C. (2009). Antitumor activity of the selective MDM2 antagonist Nutlin-3 against chemoresistant neuroblastoma with wild-type p53. JNCI Journal of the National Cancer Institute.

Vaseva, A. V., and Moll, U. M. (2009). The mitochondrial p53 pathway. Biochim Biophys Acta 1787, 414-420.

Vassilev, L., Vu, B., Graves, B., Carvajal, D., Podlaski, F., Filipovic, Z., Kong, N., Kammlott, U., Lukacs, C., and Klein, C. (2004). In vivo activation of the p53 pathway by small-molecule antagonists of MDM2. Science 303, 844.

Vijayalakshmi, S., Rao, R. B., Karle, I. L., and Balaram, P. (2000). Comparison of helix-stabilizing effects of alpha, alpha-dialkyl glycines with linear and cycloalkyl side chains. Biopolymers 53, 84-98.

Walensky, L. D., Kung, A. L., Escher, I., Malia, T. J., Barbuto, S., Wright, R. D., Wagner, G., Verdine, G. L., and Korsmeyer, S. J. (2004). Activation of apoptosis in vivo by a hydrocarbon-stapled BH3 helix. Science 305, 1466-1470.

Weir, B., Woo, M., Getz, G., Perner, S., Ding, L., Beroukhim, R., Lin, W., Province, M., Kraja, A., and Johnson, L. (2007). Characterizing the cancer genome in lung adenocarcinoma. Nature 450, 893-898.

Wilder, P. T., Rustandi, R. R., Drohat, A. C., and Weber, D. J. (1998). S100B(betabeta) inhibits the protein kinase C-dependent phosphorylation of a peptide derived from p53 in a Ca2+-dependent manner. Protein Sci 7, 794-798.

Wüthrich, K., Billeter, M., and Braun, W. (1984). Polypeptide secondary structure determination by nuclear magnetic resonance observation of short proton-proton distances*1. Journal of molecular biology 180, 715-740.

We claim:

1. A synthetic peptide comprising Sequence SEQ ID NO: 10.

2. A pharmaceutical composition comprising a therapeutically effective amount of the synthetic peptide as claimed in claim 1 as an active ingredient optionally along with at least one pharmaceutically acceptable peptide stabilizer and excipients.

3. A composition as claimed in claim 2, further comprising at least one approved chemotherapeutic agent.

4. A composition as claimed in claim 2, wherein the said composition comprises 20% to 80% (w/w) of said synthetic peptide.

5. A composition as claimed in claim 2, wherein the said composition is formulated for oral, parental, subcutaneous, intravenous or intra-articular administration.

6. A composition as claimed in claim 2, wherein the said composition is administered in the dosage of approximately 50 mg/kg body weight per day for a period of 1 to 7 days.

7. A method of making a medicament for the treatment of S100B over-expressing and/or p53 under-expressing human cancers comprising the step of formulation of a composition of claim 2.

8. A method for the treatment of human cancers having over-expression of S100B and/or down-regulation of p53 comprising administering a therapeutically effective amount of the composition as claimed in claim 2 to a patient in need thereof, wherein said cancers comprises melanoma.

9. A method as claimed in claim 8, wherein the composition is administered parenterally, subcutaneously, intravenously or intraarticularly.

10. A method as claimed in claim 8, wherein the composition is administered in a dosage of about 50 mg/kg body weight per day for a period of 1 to 7 days.

11. A method as claimed in claim 8, wherein the composition is administered in conjunction with a standard method of care including chemotherapy, radiation therapy and surgery.

* * * * *

SEQUENCE LISTING

```
<160> NUMBER OF SEQ ID NOS: 13

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

Thr Arg Thr Lys Ile Asp Trp Asn Lys Ile Leu Ser
1               5                   10

<210> SEQ ID NO 2
<211> LENGTH: 17
<212> TYPE: PRT
<213> ORGANISM: Artificial Sequence
<220> FEATURE:
<223> OTHER INFORMATION: Synthetic

<400> SEQUENCE: 2

Thr Arg Thr Lys Ile Asp Trp Asx Lys Ile Leu Asx Gly Gly Gly Cys
1               5                   10                  15
```

Gly

<210> SEQ ID NO 3
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Xaa is 6-aminohexanoic acid

<400> SEQUENCE: 3

Thr Arg Thr Lys Ile Asp Trp Asx Lys Ile Leu Asx Lys Xaa
1               5                   10

<210> SEQ ID NO 4
<211> LENGTH: 20
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Xaa is 6-aminohexanoic acid

<400> SEQUENCE: 4

Arg Arg Arg Arg Arg Arg Thr Arg Thr Lys Ile Asp Trp Asx Lys Ile
1               5                   10                  15

Leu Asx Lys Xaa
            20

<210> SEQ ID NO 5
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Xaa is 6-aminohexanoic acid

<400> SEQUENCE: 5

Thr Arg Thr Lys Ala Asp Ala Asx Lys Ile Leu Asx Lys Xaa
1               5                   10

<210> SEQ ID NO 6
<211> LENGTH: 15
<212> TYPE: PRT
<213> ORGANISM: Artificial Sequence
<220> FEATURE:
<223> OTHER INFORMATION: Synthetic

<400> SEQUENCE: 6

Gln Ser Thr Ser Arg His Lys Lys Leu Met Phe Lys Thr Glu Gly
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic

<400> SEQUENCE: 7

Gln Ser Thr Asx Arg His Asx Lys Leu Met Phe Lys Thr Asx Gly
1               5                   10                  15

<210> SEQ ID NO 8
<211> LENGTH: 19
<212> TYPE: PRT
<213> ORGANISM: Artificial Sequence
<220> FEATURE:
<223> OTHER INFORMATION: Synthetic

<400> SEQUENCE: 8

Gln Ser Thr Asx Arg His Asx Lys Leu Met Phe Lys Thr Asx Gly Gly
1               5                   10                  15

Gly Cys Gly

<210> SEQ ID NO 9
<211> LENGTH: 25
<212> TYPE: PRT
<213> ORGANISM: Artificial Sequence
<220> FEATURE:
<223> OTHER INFORMATION: Synthetic

<400> SEQUENCE: 9

Arg Arg Arg Arg Arg Arg Gln Ser Thr Asx Arg His Asx Lys Leu Met
1               5                   10                  15

Phe Lys Thr Asx Gly Gly Gly Cys Gly
            20                  25

<210> SEQ ID NO 10
<211> LENGTH: 41
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (20)..(20)
<223> OTHER INFORMATION: Xaa is 6-aminohexanoic acid
<220> FEATURE:
<221> NAME/KEY: misc_feature
<222> LOCATION: (22)..(22)
<223> OTHER INFORMATION: Xaa is 6-aminohexanoic acid

<400> SEQUENCE: 10

Arg Arg Arg Arg Arg Arg Thr Arg Thr Lys Ile Asp Trp Asx Lys Ile
1               5                   10                  15

Leu Asx Lys Xaa Lys Xaa Lys Asx Leu Ile Lys Asx Trp Asp Ile Lys
            20                  25                  30

Thr Arg Thr Arg Arg Arg Arg Arg Arg
            35                  40

<210> SEQ ID NO 11
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Xaa is 6-aminohexanoic acid
<220> FEATURE:
<221> NAME/KEY: misc_feature
<222> LOCATION: (16)..(16)
<223> OTHER INFORMATION: Xaa is 6-aminohexanoic acid

<400> SEQUENCE: 11

```
Thr Arg Thr Lys Ile Asp Trp Asx Lys Ile Leu Asx Lys Xaa Lys Xaa
1               5                   10                  15

Lys Asx Leu Ile Lys Asx Trp Asp Ile Lys Thr Arg Thr
            20                  25

<210> SEQ ID NO 12
<211> LENGTH: 29
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (14)..(14)
<223> OTHER INFORMATION: Xaa is 6-aminohexanoic acid
<220> FEATURE:
<221> NAME/KEY: misc_feature
<222> LOCATION: (16)..(16)
<223> OTHER INFORMATION: Xaa is 6-aminohexanoic acid

<400> SEQUENCE: 12

Thr Arg Thr Lys Ala Asp Ala Asx Lys Ile Leu Asx Lys Xaa Lys Xaa
1               5                   10                  15

Lys Asx Leu Ile Lys Asx Ala Asp Ala Lys Thr Arg Thr
            20                  25

<210> SEQ ID NO 13
<211> LENGTH: 23
<212> TYPE: PRT
<213> ORGANISM: Artificial Sequence
<220> FEATURE:
<223> OTHER INFORMATION: Synthetic

<400> SEQUENCE: 13

Arg Arg Arg Arg Arg Arg Thr Arg Thr Lys Ile Asp Trp Asx Lys Ile
1               5                   10                  15

Leu Asx Gly Gly Gly Cys Gly
            20
```